United States Patent
Stiger et al.

(10) Patent No.: US 6,746,392 B2
(45) Date of Patent: Jun. 8, 2004

(54) BRACHYTHERAPY CATHETER WITH TWISTED LUMENS AND METHODS OF USE

(75) Inventors: Mark L. Stiger, Santa Rosa, CA (US); Sam Ciamacco, Jr., San Diego, CA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 367 days.

(21) Appl. No.: 09/885,112

(22) Filed: Jun. 20, 2001

(65) Prior Publication Data

US 2002/0198432 A1 Dec. 26, 2002

(51) Int. Cl.$^7$ ................................................. A61N 5/00
(52) U.S. Cl. ...................... 600/3; 604/93.01; 604/510
(58) Field of Search ................ 600/1, 3, 7, 8; 604/93.07, 96.01, 103.1, 508, 509, 510

(56) References Cited

U.S. PATENT DOCUMENTS

| | | |
|---|---|---|
| 4,795,439 A | 1/1989 | Guest |
| 5,383,856 A * | 1/1995 | Bersin .................... 604/101.01 |
| 5,882,290 A | 3/1999 | Kume |
| 5,891,091 A | 4/1999 | Teirstein |
| 5,910,101 A | 6/1999 | Andrews et al. |
| 5,938,582 A | 8/1999 | Ciamacco, Jr. et al. |
| 5,947,924 A | 9/1999 | Liprie |
| 5,951,458 A | 9/1999 | Hastings et al. |
| 5,976,106 A | 11/1999 | Verin et al. |
| 6,024,690 A | 2/2000 | Lee et al. |
| 6,033,357 A | 3/2000 | Ciezki et al. |
| 6,048,299 A | 4/2000 | Hoffmann |
| 6,059,713 A | 5/2000 | Urick et al. |
| 6,059,812 A | 5/2000 | Clerc et al. |
| 6,074,338 A | 6/2000 | Popowski et al. |
| 6,074,339 A | 6/2000 | Gambale et al. |
| 6,077,213 A | 6/2000 | Ciezki et al. |
| 6,093,142 A | 7/2000 | Ciamacco, Jr. |
| 6,099,454 A | 8/2000 | Hastings et al. |
| 6,099,499 A | 8/2000 | Ciamacco, Jr. |
| 6,110,097 A | 8/2000 | Hastings et al. |
| 6,117,065 A | 9/2000 | Hastings et al. |
| 6,117,386 A | 9/2000 | Stiger |
| 6,142,926 A | 11/2000 | Schneiderman |
| 6,149,574 A | 11/2000 | Trauthen et al. |
| 6,159,140 A | 12/2000 | Loeffler et al. |
| 6,176,821 B1 | 1/2001 | Crocker et al. |
| 6,196,963 B1 | 3/2001 | Williams |

FOREIGN PATENT DOCUMENTS

| | | |
|---|---|---|
| EP | 0386408 A1 | 9/1990 |
| EP | 0 593 136 B1 | 3/1997 |
| EP | 0 810 004 A2 | 12/1997 |
| WO | WO 98/49933 A1 | 11/1998 |

* cited by examiner

*Primary Examiner*—Edward K. Look
*Assistant Examiner*—Thor Campbell

(57) ABSTRACT

An over-the-wire catheter provides substantially shadow-free delivery of radiation to a body lumen by having a treatment region wherein a guidewire tube and a radiation source tube form a parallel double helix configuration. When a radiation source is inserted into the radiation source tube and a guidewire is present in the guidewire tube, no portion of the treatment site will be obscured from all radiation emitted by the radiation source because, within the treatment region, the guidewire and the radiation source are not in a conventional, axially parallel configuration. Optionally, a balloon may be mounted about or adjacent the treatment region of the catheter, the balloon providing centering and/or dilatation functions.

4 Claims, 4 Drawing Sheets

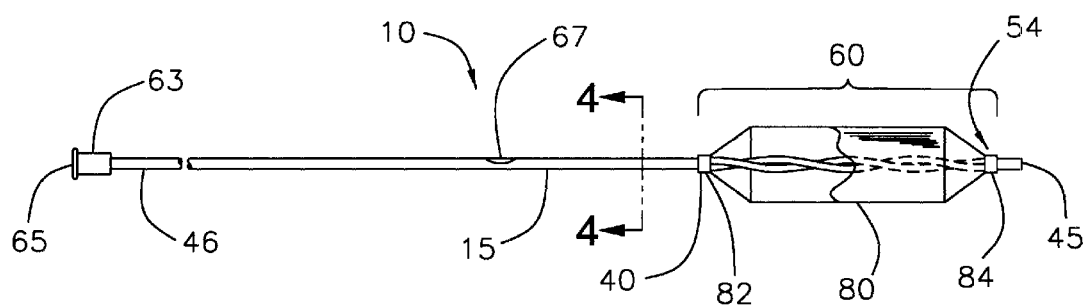
FIG. 3
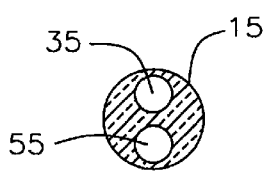    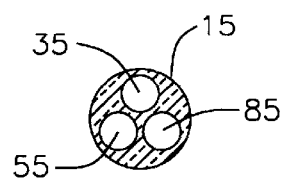    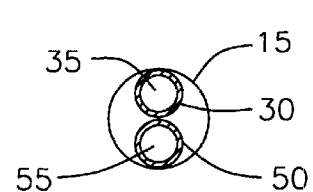
FIG. 4A          FIG. 4B          FIG. 4C

BRACHYTHERAPY CATHETER WITH TWISTED LUMENS AND METHODS OF USE

FIELD OF THE INVENTION

The present invention relates to intraluminal radiation delivery (IRT) devices and more particularly to an over-the-wire brachytherapy catheter. Also provided are methods for delivering localized radiation in vivo.

BACKGROUND OF THE INVENTION

Stenosis is a narrowing or constriction of a duct or canal. A variety of disease processes, such as atherosclerotic lesions, immunological reactions, congenital abnormalities and the like, can lead to stenoses of arteries or ducts. In the case of stenosis of a coronary artery, this typically leads to myocardial ischemia. Percutaneous transluminal coronary angioplasty (PTCA), the insertion and inflation of a balloon catheter in a coronary artery to affect its repair, is widely accepted as an option in the treatment of obstructive coronary artery disease. In general, PTCA is used to increase the lumen diameter of a coronary artery that is partially or totally obstructed by a build-up of cholesterol fats or atherosclerotic plaque. In PTCA, a coronary guiding catheter provides a channel from outside the patient to the ostium of a coronary artery. Then, a balloon catheter is advanced over a small diameter, steerable guidewire through the guiding catheter, into the artery, and across the stenosis. The balloon is inflated to expand the narrowing. Dilatation of the occlusion, however, can form flaps, fissures and dissections which threaten abrupt reclosure of the dilated vessel or even perforations in the vessel wall. To treat or prevent such sequelae, tubular stents are often placed within the angioplasty site to scaffold the vessel lumen.

Other invasive vascular therapies include atherectomy (mechanical removal of plaque residing inside an artery), laser ablative therapy and the like. While the stenosis or occlusion is greatly reduced using these therapies, many patients experience a recurrence of the stenosis over a relatively short period. Restenosis, defined angiographically, is the recurrence of a 50% or greater narrowing of a luminal diameter at the site of a prior therapy. Additionally, researchers have found that angioplasty or placement of a stent in the area of the stenosis can irritate the blood vessel and cause rapid reproduction of the cells in the medial layer of the blood vessel, developing restenosis through a mechanism called medial hyperplasia. Restenosis is a major problem which limits the long-term efficacy of invasive coronary disease therapies. Additionally, the rapid onset of restenosis is compounded by the lack of ability to predict which patients, vessels, or lesions will undergo restenosis.

Although the mechanism of restenosis is not fully understood, clinical evidence suggests that restenosis results from a migration and rapid proliferation of a subset of predominately medially derived smooth muscle cells, which is apparently induced by the injury from the invasive therapy. Such injury, for example, is caused by the angioplasty procedure when the balloon catheter is inflated and exerts pressure against the artery wall, resulting in medial tearing. It is known that smooth muscle cells proliferate in response to mechanical stretch and the resulting stimulation by a variety of growth factors. Also, intimal hyperplasia can contribute to restenosis, stimulated by the controlled therapeutic injury. It is believed that such proliferation stops one to two months after the initial invasive therapy procedure but that these cells continue to express an extracellular matrix of collagen, elastin and proteoglycans. Additionally, animal studies have shown that during balloon injury, denudation of endothelial cells can occur, followed by platelet adhesion and aggregation, and the release of platelet-derived growth factor (PDGF) as well as other growth factors. As mentioned above, this mass of tissue can contribute to the re-narrowing of the vascular lumen in patients who have restenosis. It is believed that a variety of biologic factors are involved in restenosis, such as the extent of the tissue injury, platelets, inflammatory cells, growth factors, cytokines, endothelial cells, smooth muscle cells, and extracellular matrix production, to name a few.

It has been found that irradiating the blood vessel walls at the treatment site can reduce or prevent hyperplasia. Precise control over the amount of radiation is important, since insufficient radiation will not prevent restenosis and excessive radiation can further damage the blood vessel or surrounding tissues. To prevent unnecessary radiation beyond the site of the stenosis, it is preferable to introduce a small radiation source into the treated vessel. The prior art contains numerous examples of radiation catheters and source wires for this purpose.

One prior art device describes a catheter having a spherical inflatable chamber adjacent the catheter distal end. A fluid containing a radioactive material such as radioactive iodine is pumped into the chamber, inflating the chamber and treating the vessel walls with ionizing radiation. The chamber will stop blood flow, so it can be inflated only for a short time. Further, precisely controlling radiation exposure and fully draining the chamber to end treatment are very difficult.

Another prior art catheter includes radiation means positioned in an elongate, flexible carrier. The carrier lacks any provision for steering or for over-the wire guidance, which is necessary for negotiating tortuous and branching vessels. Another prior art device mounts a radiation source distally on or within a guidewire.

Other prior art catheters include one or more balloons used to center a radiation source within the vessel. Irradiating a segment of an artery or the like generally takes from about 3 to 45 minutes. Since a balloon typically occludes, or shuts off blood flow through an artery, treatment can be conducted for only short periods before ischemia or tissue damage from lack of blood flow becomes significant. To solve this problem, some balloon-centered radiation catheters include a bypass, or perfusion feature, so that blood continues to flow through the artery during treatment. In some devices, the perfusion feature is provided by mounting a helical centering balloon around the catheter shaft. During radiation treatment, the helical balloon is inflated to center the catheter shaft in the vessel and to allow blood to flow through the spiral channel formed between the helical turns of the balloon. In alternative prior art devices, the catheter shaft is mounted off-center within a helical balloon such that blood can flow through the center of the helix.

Yet another prior art radiation catheter includes a first guidewire lumen, a second blind lumen to receive a radiation source wire, and an inflatable centering member that permits blood flow therethrough during radiation treatment. However, since the two lumens extend parallel to each other and to the axis of the catheter, the guidewire will block radiation from the source wire, forming a linear shadow along the wall of the vessel. This shadowing phenomenon typically requires that the guidewire be withdrawn from the treatment site to ensure that radiation emitted by the source is not blocked by the guidewire. Withdrawing the guidewire adds time to the procedure. Also, when using a rapid-exchange type catheter, with the attendant short guidewire lumen, withdrawing the guidewire brings the risk of having the guidewire slip out of the catheter completely. In this untoward event, the guidewire cannot be reinserted into the catheter without removing both devices from the patient.

With the above in mind, it is an object of the invention to provide an over-the-guidewire radiation catheter that can deliver a shadow-free dose of therapeutic radiation to a treatment site without requiring withdrawal of the guidewire.

SUMMARY OF THE INVENTION

The present invention is a transluminal, over-the-wire catheter that provides a lumen for guiding a radiation source wire to an intended treatment site within a patient. With the removable radiation source wire in place, the catheter provides shadow-free irradiation of an intended vessel wall without having to move or withdraw the guidewire. Although the guidewire lies within the radiation pattern emitted by the radiation source wire, the guidewire does not cast a linear radiation shadow on the vessel wall because the guidewire and the radiation source wire are arranged in a parallel double helix configuration. The catheter of the invention includes a first lumen for the guidewire and a second lumen for the radiation source wire. The two lumens are twisted together to form the desired parallel double helix configuration for the guidewire and the radiation source wire.

An optional embodiment of the invention provides a centering mechanism to keep the double helix configuration centered in the vessel being treated. The centering mechanism may be an inflatable balloon mounted around the catheter shaft adjacent the distal end of the catheter. The balloon is inflated through a third lumen that extends from the proximal end of the catheter to the balloon. The centering balloon may comprise a single elongate balloon, which may be a dilatation balloon. Other centering balloons may be a helical or spiral balloon, a multi-lobed balloon, or two or more short, catenated balloons. Some of these balloon variations are better suited for treatment in a vessel having a tight radius bend, and others permit perfusion of blood past the centering mechanism, both concepts being understood by those of skill in the art of radiation catheters. Other optional centering mechanisms may include wire braid structures or wire hoops mounted about the double helix configuration at the distal end of the catheter.

The catheter of the invention may also incorporate a dilatation balloon mounted about or adjacent to the double helix configuration. In this alternate embodiment, the balloon may be used to perform angioplasty before, or concomitantly with intravascular radiotherapy provided from the double helix configuration.

Although catheters in accordance with the invention are well suited for the treatment of coronary arteries, any body lumen can be treated by a medical device of the present invention, including the vas deferens, ducts of the gallbladder, prostate gland, trachea, bronchus and liver or larger, peripheral arteries.

BRIEF DESCRIPTION OF THE DRAWINGS

These and other features, aspects and advantages of the present invention will become better understood with reference to the following description, appended claims, and accompanying drawings where:

FIG. 3 is a fragmented elevational view of a radiation catheter in accordance with the present invention;

FIG. 4A is a transverse sectional view of a catheter according to the invention, taken on line 4—4 of FIG. 3;

FIG. 4B is a transverse sectional view of a catheter according to an alternative embodiment of the invention, taken on line 4—4 of FIG. 3;

FIG. 4C is a transverse sectional view of a catheter according to another alternative embodiment of the invention, taken on line 4—4 of FIG. 3;

DESCRIPTION OF THE PREFERRED EMBODIMENTS

An apparatus is provided by the present invention that allows for intraluminal radiation therapy (IRT). Preferably, the apparatus is a catheter including a pair of elongate tubes, wherein a guidewire tube and a radiation source tube are arranged in a twisted configuration over at least a portion of the catheter. With a linear radiation filament, or source wire and a guidewire traversing the respective tubes, a substantially uniform radiation dose can be delivered to an in vivo treatment site. The guidewire will not "shadow" or block the radiation emitted from the radioactive source wire because these wires will alternate coaxially along the portion of the catheter having the twisted configuration.

Figure 1:
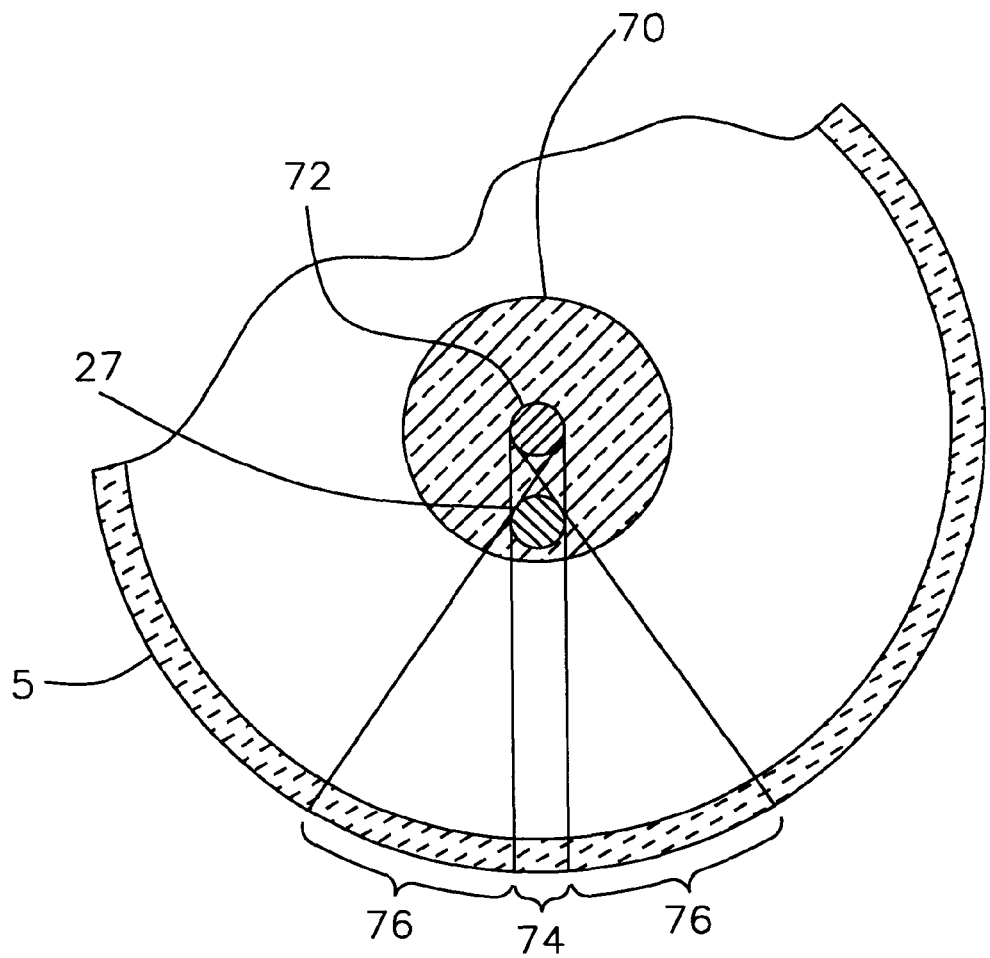
FIG. 1 is a partial transverse cross-sectional illustration of a prior art radiation catheter deployed in a vessel of a patient.
Figure 2:
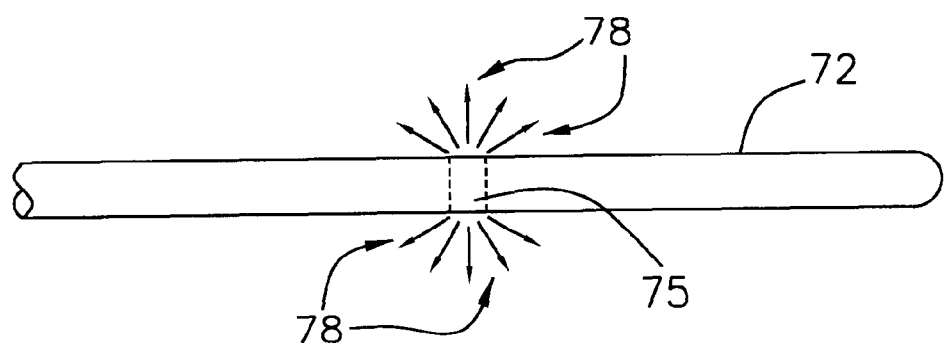
FIG. 2 is an elevational view of a distal section of a prior art radiation source wire, showing the radiation pattern emitted by a short section thereof.

FIG. 1 illustrates the shadowing problem solved by the present invention. Prior art radiation catheter 70 is shown as being generally centered in vessel 5. Radiation source wire 72 and guidewire 27 are located within catheter 70, which is transparent to radiation emitted by source wire 72. As shown in FIG. 2, each short, or point segment 75 of radiation source wire 72 emits radiation along omnidirectional rays 78. Stacking a series of such segments 75 proximate each other results in a cylindrical radiation pattern (not shown). For a point source, the radiation density varies inversely with the square of the distance therefrom. Arranging a series of point sources to form a linear source, such as source wire 72, results in the radiation density varying inversely with the distance therefrom.

Because guidewire 27 and source wire 72 are arranged parallel to each other and to the central axis of prior art catheter 70, linear umbra 74 is formed along vessel 5 by guidewire 27. Penumbras 76 are also formed adjacent the sides of umbra 74. Thus, linear umbra 74 receives no radiation, penumbras 76 receive a partial dose of radiation, and the remainder of vessel 5 receives a uniform, full dose of radiation from source wire 72. Such non-uniform radiation treatment around the circumference of the vessel may be expected to achieve less than ideal results, especially because some tissue (within umbra 74) receives no radiation at all. The only way to avoid this shortcoming of catheter 70 during use is to withdraw guidewire 27 from the treatment area.

FIG. 3 shows a medical device in accordance with the invention, such as radiation catheter 10, which includes elongate body 15, proximal end 46 and distal end 45. Guidewire lumen 35 and radiation source lumen 55 both extend through body 15, as shown in FIGS. 4A–4C. Fitting 63 is affixed to proximal end 46, in communication with lumen 55, and optionally with lumens 35, 85, as will be discussed below. Catheter body 15 may be formed from a two-lumen extrusion, as shown in FIG. 4A, a three-lumen extrusion, as shown in FIG. 4B, or by joining two parallel, single-lumen tubes 30, 50, as shown in FIG. 4C. Treatment region 60 is disposed adjacent distal end 45, and comprises an arrangement of lumens 35, 55 in a parallel double helix configuration. The double helix configuration is preferably formed by twisting parallel, single-lumen tubes 30, 50. Preferably, treatment region 60, formed by twisted tubes, is joined to the remainder of body 15, which comprises a two-lumen extrusion. Lumens 35, 55 are sized to slidably receive guidewire 27 and radiation source wire 72, respectively.

In a first alternative embodiment, all of body 15, including treatment region 60, can be formed by joining parallel tubes 30, 50. In a second alternative embodiment, all of body 15, including treatment region 60, can be formed from a two-lumen extrusion. It is to be understood that the double helix configuration of lumens 35, 55 is formed at least in the treatment region 60, although the double helix configuration may form substantially the entire length of catheter 10. The double helix may also be considered as a bifilar helix, wherein two helical elements are arranged in parallel relationship with spaced apart helical turns in each element, the turns being in the same direction and having a generally constant phase relationship, and the turns of one helical element being located between the spaced turns of the other helical element.

In the preferred structure shown in FIG. 3, tubes 30, 50 form a closed double helix within treatment region 60, where the term "closed" means tubes 30, 50 are in continuous longitudinal contact with each other across a central axis of the device, as shown in FIG. 4C. Incorporating a closed double helix configuration into catheter 10 results in treatment region 60 having a maximum transverse dimension that is substantially equal to the maximum transverse dimension of the remainder of catheter body 15 proximal of treatment region 60. In an alternative embodiment, not shown, tubes 30, 50 can form a relatively larger diameter, open double helix, wherein tubes 30, 50 are spaced apart across the central axis of treatment region 60. Incorporating an open double helix configuration into catheter 10 would result in treatment region 60 having a maximum transverse dimension that is larger than the maximum transverse dimension of the remainder of catheter body 15 proximal of treatment region 60. Lumens 35, 55 may be twisted during extrusion of tubing to form all or portions catheter body 15, as will be understood by those skilled in the art of catheter extrusion. Alternatively, suitable catheter tubing can be formed with straight lumens, all or portions of which can be twisted and heat set in a secondary operation. Optionally, tubes 30, 50 can be extruded separately, then joined side-by-side to form two-lumen tubing using a suitable adhesive, solvent bonding or heat bonding techniques.

Optionally, a centering mechanism is mounted about treatment region 60, as shown in FIG. 3. Preferably, the centering mechanism comprises inflatable balloon 80, which is fixed to body 15 with balloon proximal neck 82 and balloon distal neck 84. As shown in FIG. 4B, inflation lumen 85 extends through body 15 to communicate between proximal fitting 63 and balloon 80. Centering balloon 80 may comprise a single elongate balloon of either an elastic material, or preferably of a high strength, inelastic material forming a dilatation type balloon. Typical thermoplastic polymers used to stretch blow-mold the dilatation balloon are polyolefins, polyamides, polyethylene terephthalate (PET), and block copolymers such as PEBAX®, a polyether block amide from Elf Atochem North America, Inc., Philadelphia, Pa., U.S.A. If centering balloon 80 is a dilatation balloon, then the interventionist has the option of simultaneously performing PTCA and brachytherapy on a vascular stenosis.

Centering balloon 80 may also be a helical or spiral balloon, a multi-lobed balloon, or two or more short, catenated balloons. Some of these balloon variations are better suited for treatment in vessels having a tight radius bend, and others permit blood to perfuse past the centering mechanism while it is inflated, both concepts being understood by those of skill in the art of brachytherapy catheters. Other optional centering mechanisms may include wire braid structures or wire hoops mounted about treatment region 60.

Figure 5:
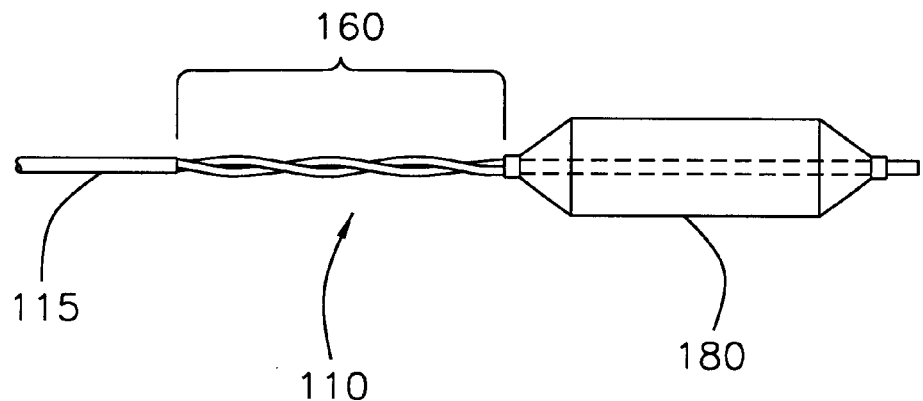
FIG. 5 is a partial illustration of a catheter in accordance with an alternative embodiment of the invention.

FIG. 5 shows an alternative embodiment of a medical device in accordance with the invention, wherein catheter 110 includes elongate body 115, dilatation balloon 180, and treatment region 160. The structural elements of catheter 110 are similar to the elements of catheter 10, however, treatment region 160 is located proximal to balloon 180 instead of these two elements being coaxially arranged. Catheter 110 permits intravascular radiotherapy immediately following PTCA, without having to exchange catheters. Optionally, treatment region 160 can be located distal to balloon 180, where its relatively lower profile and greater flexibility can be advantageous for negotiating narrow vessels.

Figure 6:
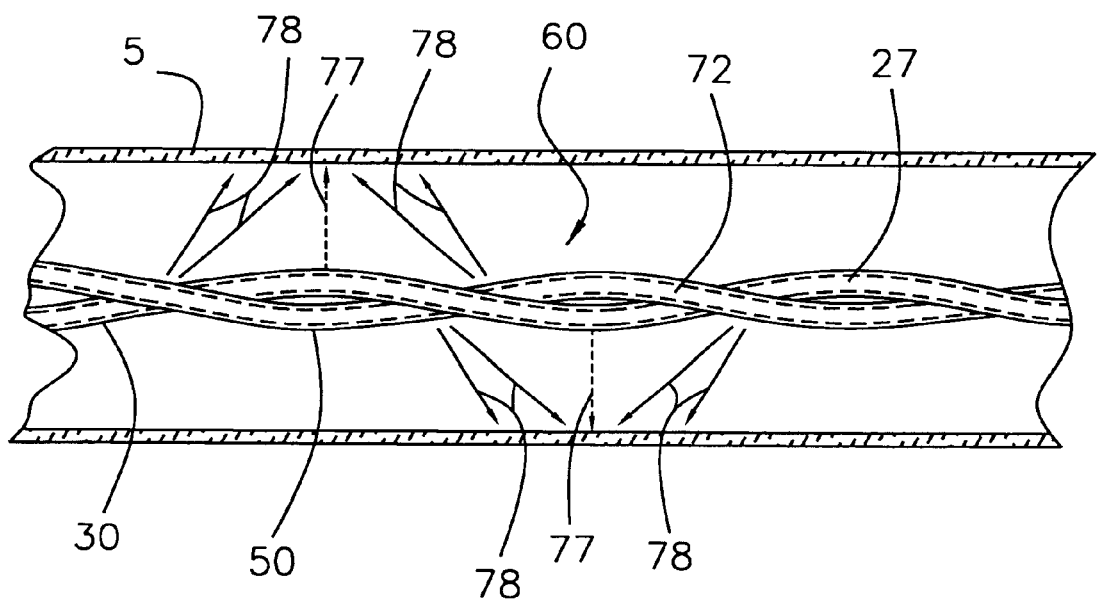
FIG. 6 is a partial illustration of a catheter in accordance with the invention deployed within a portion of a vessel.

FIG. 6 illustrates how the double helix arrangement of the invention provides shadow-free irradiation of vessel 5. Treatment region 60 is shown generally centered in vessel 5, as by optional centering balloon 80 (not shown in FIG. 6). Guidewire 27 and radiation source wire 72 lie within tubes 30, 50, respectively. Although emission along (broken) rays 77 is blocked by guidewire 27, emission along omnidirectional rays 78 from adjacent portions of source wire 72 is not blocked, and will irradiate the areas that cannot be reached along rays 77. Essentially, the twisting paths of catheter tubes 30, 50 through treatment region 60 retain guidewire 27 displaced from a linear blocking position, and further hold source wire 72 in a helically adjacent emission position, from which source wire 72 can irradiate the entire target site, including any tissue that would lie in the direct shadow of guidewire 27. Although some portions of vessel 5 may lie within a penumbra, the invention creates no umbra beyond guidewire 27. Thus, all of the tissue that is intended to be treated receives at least a some portion of the radiation emitted by source wire 72.

A catheter according to the present invention is preferably provided with a conventional "rapid exchange" or "single operator exchange" feature. In general, exchanging catheters having full-length lumens over exchange-length guidewires is difficult because such procedures require at least two operators who must be in communication during the procedure, requiring more time and increasing the likelihood of contamination by dropping the guidewire from the sterile field, for example. Thus, rapid exchange catheters include a short guidewire lumen that enables a single operator to anchor or hold a standard-length guidewire when the catheter is removed from the body with the exchange occurring over the short guidewire portion that extends from the patient.

In the preferred rapid-exchange embodiment shown in FIG. 3, guidewire exit port 67 is typically located at such a point along the length of the catheter so as to limit the guidewire length necessary to position a radiation treatment portion of the catheter in close proximity to an in vivo treatment site, such as about 20 cm from distal end 45 of catheter 10. Guidewire 27 can enter distal end 45, pass through guidewire lumen 35, and exit from port 67. In the rapid exchange embodiment shown in FIG. 3, the portion of body 15 proximal to port 67 can lack guidewire lumen 35, since the guidewire does not extend through this portion of catheter 10. Alternatively, a conventional over-the-wire configuration may also be included wherein the guidewire lumen 35 runs substantially the entire length of catheter 10, and wherein port 67 would be located in fitting 63. It is to be understood that, since rapid exchange catheters utilize guidewires, these devices are considered to be a subset of over-the-wire catheters.

Radiation source lumen 55 extends from proximal end 46, where it communicates with radiation port 65 in fitting 63, at least through treatment portion 60 to termination point 54 at or near distal end 45. Preferably, radiation source lumen 55 is closed at termination point 54. Radiation source lumen 55 provides a passage through which radiation source wire 72 can be slidably positioned.

Radiopaque marker 40 is preferably provided and can be attached at one or more locations along catheter body 15. Preferably, at least one location of radiopaque marker 40 is adjacent the proximal end of treatment region 60. As shown in FIG. 3, marker 40 may be about, within, or adjacent balloon proximal neck 82. Radiopaque marker 40 is used to provide a fluoroscopic indication of the location of the treatment region 60, thus allowing the operator to adjust the position of the treatment region 60 in proximity to the in vivo site targeted for therapy. Radiopaque markers are commonly made from metals having high X-ray attenuation coefficients, such as gold or platinum, or alloys thereof.

In the present invention, catheters 10, 110 are preferably formed from any materials that are biocompatible, are biostable, and minimize irritation to the body passageway during treatment. Such materials may include a polymer, a metal, or combinations thereof. Biocompatible and biostable polymers are those which stimulate a relatively low chronic tissue response. Preferably, polymer materials used are radiolucent and may also be optically transparent. Suitable polymers can be selected from the group comprising a polyurethane, a silicone, a polyester, a polyolefin, a block copolymer and other thermoplastic or thermoset plastic materials known to be suitable for construction of medical devices. Although catheters 10, 110 can incorporate metals such as stainless steel or shape memory alloys such as nitinol, these materials should be avoided when forming at least treatment regions 60, 160 of bodies 15, 115 respectively, where the metal could block the intended emission of radiation.

The diameter of guidewire lumen 35 typically measures about 0.41 mm (0.016 inch) for guidewires having a diameter of about 0.36 mm (0.014 inch), depending upon the intended clinical application for catheters 10, 110. For example, smaller diameters may be used in neurovascular applications, while larger diameters may be used in peripheral artery applications. The diameter of radiation source lumen 55 typically is as small as possible while still accommodating a linear radiation source such as source wire 72. The diameters of guidewire lumen 35 and radiation source lumen 55 can be the same or different, depending upon the application.

Figure 7:
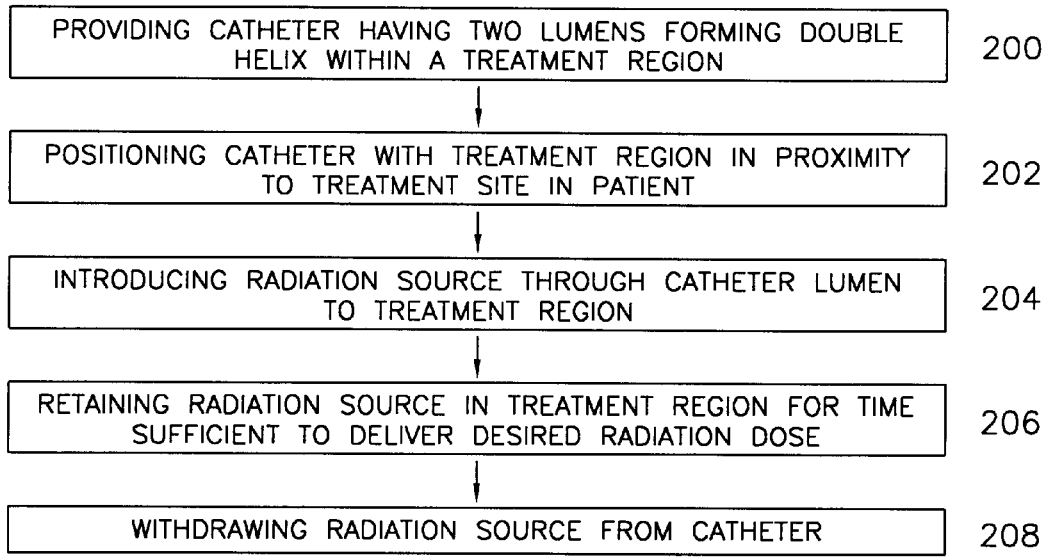
FIG. 7 is a flow chart depicting a method of using a catheter of the present invention.

According to a method of using the invention, as shown in FIG. 7, catheter 10 is percutaneously inserted into the patient's vessels, preferably traversing a vein or artery until treatment region 60 of catheter 10 reaches the desired site for radiation therapy (steps 200, 202). Radiation source wire 72, having a radioactive portion, typically including an isotope, is introduced through source lumen 55 until the radioactive portion enters treatment region 60 of catheter 10 (step 204). The radioactive portion remains within treatment region 60 for a desired period of time, depending upon the prescribed treatment dose (step 206).

It is preferred that a low dose of radiation is delivered for a sufficient period of time to suppress the proliferative response to injury in vivo. Thus, total dose (generally measured in centi Gray) is typically determined by the specific activity of the radiation emitting material (generally measured in micro Curies ($\mu$Ci)) multiplied by time. However, the total dose must be balanced between the desired interruption of an injury response versus the detrimental mutagenic effect of tissue exposure to excessive radiation. Suitable radioactive materials include beta emitting isotopes (e.g., $Sr^{90}$, $Yt^{90}$, or $p^{32}$) or gamma emitting isotopes (e.g., an iridium isotope). Once treatment is complete, radiation source wire 72 is removed through source lumen 55 (step 208), or catheter 10 and source wire 72 can be removed together. Optionally, catheter 10 includes dilatation balloon 80, mounted about treatment region 60. Radiation source wire 72 can be inserted into treatment region 60 before, during, or after the angioplasty performed with balloon 80.

Figure 8:
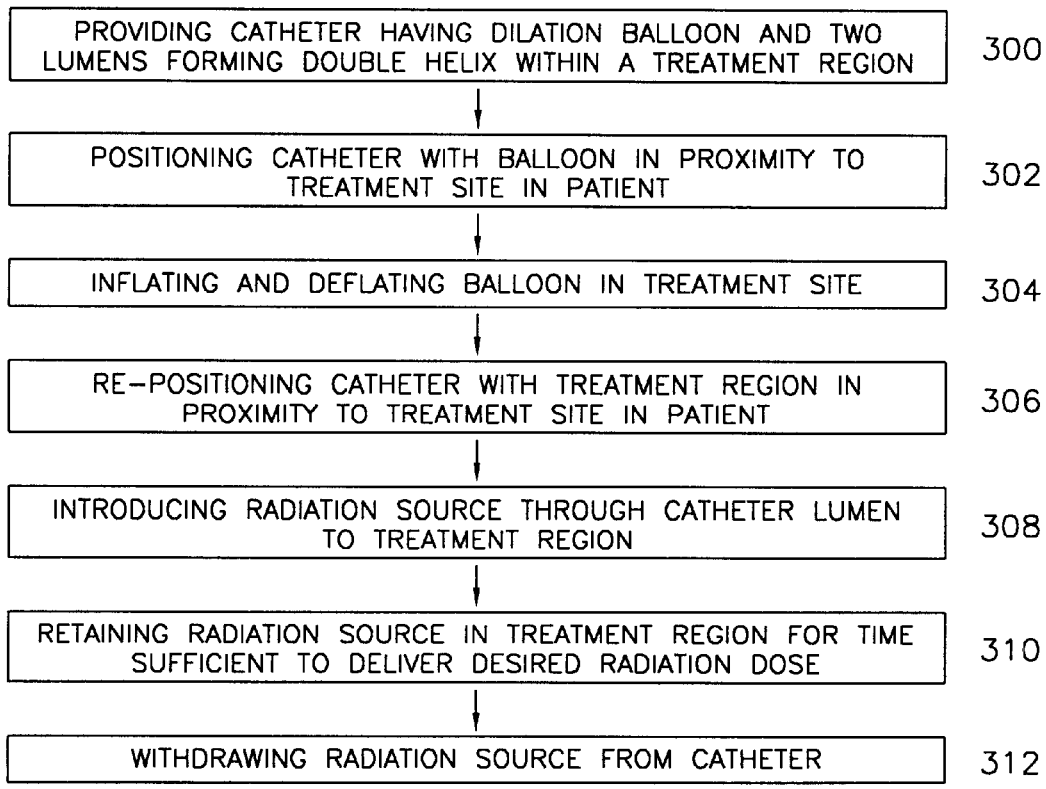
FIG. 8 is a flow chart depicting a method of using a catheter in accordance with an alternative embodiment of the present invention.

According to a method of using an alternative embodiment of the invention, as shown in FIG. 8, catheter 110 is percutaneously inserted into the patient's vessels, preferably traversing a vein or artery until dilatation balloon 180 reaches the desired treatment site (steps 300, 302). Dilatation balloon 180 is inflated and deflated (step 304) according to usual procedures for PTCA. Then, catheter 110 is re-positioned as necessary until treatment region 160 of catheter 110 lies within the treatment site (step 306). Radiation source wire 72, having a radioactive portion, typically including an isotope, is introduced through source lumen 55 until the radioactive portion enters treatment region 160 of catheter 110 (step 308). The radioactive portion remains within treatment region 160 for a desired period of time, depending upon the prescribed treatment dose (step 310).

The preceding specific embodiments are illustrative of the practice of the invention. Various modifications and alterations of this invention will become apparent to those skilled in the art without departing from the scope and spirit of this invention, and it should be understood that this invention is not to be unduly limited to illustrative embodiments set forth herein.

What is claimed is:

1. A catheter for intraluminal treatment comprising:
   an elongate catheter body having proximal and distal ends; and first and second lumens extending through the catheter body, wherein at least a portion of the first lumen and at least a portion of the second lumen are arranged in parallel relationship to form first and second helical elements, respectively, of a double helix configuration, the double helix configuration comprises at least a treatment region disposed adjacent the catheter body distal end; and
   the first lumen is adapted to slidably receive a guidewire therethrough.

2. The catheter of claim 1 wherein the first lumen extends from an entrance port at the catheter body distal end to an exit port spaced a short distance proximal of the treatment region, the exit port being spaced a substantially greater distance from the catheter body proximal end.

3. The catheter of claim 1 wherein the second lumen is adapted to slidably receive a radiation source therein.

4. The catheter of claim 3 wherein the second lumen has a closed end adjacent the catheter body distal end.

* * * * *